United States Patent [19]

Schoenwald et al.

[11] Patent Number: 5,256,698

[45] Date of Patent: Oct. 26, 1993

[54] TREATMENT OF PSYCHOSIS USING CYCLOHEXYL-PHENYL-LOWER ALKYL AMINE DERIVATIVES

[75] Inventors: Ronald D. Schoenwald; Charles F. Barfknecht, both of Iowa City, Iowa; Roger E. Newton, River Edge, N.J.

[73] Assignee: University of Iowa Research Foundation, Oakdale, Iowa

[21] Appl. No.: 557,581

[22] Filed: Jul. 24, 1990

Related U.S. Application Data

[63] Continuation-in-part of Ser. No. 257,826, Oct. 14, 1988, which is a continuation of Ser. No. 168,680, Mar. 16, 1988, Pat. No. 4,820,737, which is a continuation of Ser. No. 15,117, Feb. 17, 1987, abandoned.

[51] Int. Cl.$^5$ .............................................. A61K 31/135
[52] U.S. Cl. ................................................... 514/649
[58] Field of Search ............... 514/642, 646, 648, 649, 514/650, 651

[56] References Cited

U.S. PATENT DOCUMENTS

| | | | |
|---|---|---|---|
| 3,794,734 | 2/1974 | Cragoe | 424/330 |
| 4,018,895 | 4/1977 | Molloy et al. | 514/649 |
| 4,194,009 | 3/1980 | Molloy et al. | 514/651 |
| 4,551,473 | 11/1985 | Schossow | 514/305 |
| 4,588,746 | 5/1986 | Watthey | 514/554 |
| 4,897,425 | 1/1990 | Zipperer et al. | 514/649 |

OTHER PUBLICATIONS

Zhehyazkor, L., et al, *Compt. Rend. Acad. Bulgare Sci.*, vol. 14, pp. 607–610 (1865).
Chiavarelli, S., et al, *Gazz. Chem. ital.*, vol. 83, pp. 347–356 (1953).
C.A.: vol. 58, No. 462d (1963).
C.A.: vol. 49, No. 205h (1955).
Stedman's Medical Dictionary, 24th Ed., Williams & Wilkens, Baltimore, p. 345 (1982).
CA 51: 8287-Reiff (1956).
CA 83: 163803s-Edward (1975).

*Primary Examiner*—Frederick E. Waddell
*Assistant Examiner*—T. J. Criares
*Attorney, Agent, or Firm*—Zarley, McKee, Thomte, Voorhees, & Sease

[57] ABSTRACT

The method and composition for treating psychotic disorders with psychoactive drugs which bind at the sigma binding site and act as antagonists to inhibiting psychotic action. The preferred compounds are N-cyclohexyl-N-ethyl benzylamine, N-cyclohexyl-N-ethyl 2-phenylethylamine, and bromhexine.

7 Claims, No Drawings

TREATMENT OF PSYCHOSIS USING CYCLOHEXYL-PHENYL-LOWER ALKYL AMINE DERIVATIVES

CROSS-REFERENCE TO A RELATED APPLICATION

This application is a continuation-in-part of Ser. No. 257,826 filed Oct. 14, 1988 pending, which is a continuation of Ser. No. 168,680 filed Mar. 16, 1988, now U.S. Pat. No. 4,820,737 dated Apr. 11, 1989, which itself is a continuation of Ser. No. 015,117 filed Feb. 17, 1987, now abandoned.

BACKGROUND OF THE INVENTION

Certain compounds of low toxicity have been discovered to bind to specific molecular recognition sites (drug receptor or neurotransmitter receptor sites) within tissue. The primary area in which these discoveries have occurred has been the brain due to the high population and diversity of such sites within nervous tissue although such sites are present throughout the body. Awareness of receptor sites in the body has emerged from pharmacological studies originally intended to discover the bases of action for drugs empirically found to be useful in the treatment of various disorders. It is believed that many disorders, particularly those of the nervous system, are due to altered activity in various receptor populations. Through study of the regional distribution and activity of these varied receptor systems a picture of tissue function can be derived. The initial step in any such study involves the selection of compounds which will selectively interact with the sites of interest.

One neurotransmitter-receptor system of interest is the dopaminergic system. The relationship of the activity of this system to psychopathological symptoms is not entirely clear, however, its importance is inferred through the effectiveness of dopamine receptor antagonists in abating psychotic symptoms. A number of compounds of different classes have this desired effect and would lend themselves to adaptation for study of their sites of activity. These would include drugs of the butyrophenone class such as spiperone, haloperidol (Haldol) and droperidol; drugs of the phenothiazine class such as trifluoperazine and thiothixene; and drugs of the benzamide class such as sulpiride. Alternatively, dopamine receptor agonists, such as bromocriptine, might serve as useful ligand substrates for study of the dopaminergic system, particularly among individuals suffering from parkinsonism.

The term "ligand" is used herein to generally describe the tissue binding portion of the active molecules referred to above. It can be seen that for the most part the molecules are psychoactive drugs. However, from time to time the broader term "ligand" is used because many of the useful compounds may well be derived from psychoactive drugs, but they themselves may not be the active drug form.

Pharmacological, biochemical and behavioral characterization of sigma binding sites is currently the focus of intense, wide-spread investigation. While the precise nature of sigma binding sites in cells is not quite known, many studies have suggested that it represents the site of action for a number of important drugs. For example, haloperidol, a butyrophenone antipsychotic, exhibits high affinity for sigma binding sites and several psychotomimetics, including PCP and benzomorphane, also bind at this site. Thus, strong binding sigma agents are indicative of usefulness in the treatment of schizophrenia.

In fact, several sigma compounds have been developed as antipsychotics. It is also believed that strong sigma site binding may also indicate therapeutic targets for epilepsy and brain ischemia.

In sum, the discovery of sigma binding sites has prompted investigation into the functional role of the sites. While the functional role is not precisely understood, it is nevertheless true that binding studies have revealed sigma sites which may exhibit a unique pharmacological profile, and have provided evidence favoring the existence of a multiplicity of sigma binding sites in the central nervous system. There is therefore a continuing investigation and search for psychoactive compounds having a strong affinity for sigma binding sites.

This invention has as its primary objective the development of new psychoactive drugs having a high degree of binding affinity at sigma binding sites and which by the nature of the chemical structure have little or no likelihood of significant side affects. These compounds are thus highly useful antipsychotic drugs for treatments of certain mental disorders such as schizophrenia.

SUMMARY OF THE INVENTION

The method and composition for treating psychotic disorders such as schizophrenia. The method comprises administering as a psychoactive drug a compound selected from a group consisting of N-cyclohexyl-N-ethyl benzylamine, N-cyclohexyl-N-ethyl 2-phenylethylamine, and bromhexine or acceptable salt forms of these three compounds.

DETAILED DESCRIPTION OF THE INVENTION

Certain of the psychoactive drugs of the present invention also are opthalmically active as lacrimal secretion stimulants. Those compounds have generally described in an invention of two of the co-inventors of the present invention, Schoenwald and Barfknecht as described in U.S. Pat. No. 4,820,737 issued Apr. 11, 1989.

In its broadest sense, compounds useful in the invention of lacrimal secretions stimulants have the general formula:

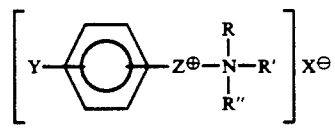

wherein Y is selected from the group consisting of hydrogen, hydroxy, halogens, amino, $C_1$ to $C_5$ alkyl, $C_1$ to $C_5$ hydroxyalkoxy and $C_1$ to $C_5$ alkoxy; Z is selected from the group consisting of $C_1$ to $C_6$ alkylene, $C_1$ to $C_6$ oxyalkylene, and $C_1$ to $C_6$ aminoalkylene; R is selected from the group consisting of $C_1$ to $C_6$ alkyl and $C_3$ to $C_7$ cycloalkyl; R' is selected from the group consisting of hydrogen, $C_1$ to $C_6$ alkyl and $C_3$ to $C_7$ cycloalkyl; R'' is selected from the group of hydrogen and $C_1$ to $C_6$ alkyl; and X is a pharmaceutically acceptable counteranion.

Y can be in either an ortho-, meta- or para- position and is preferably hydrogen. Z likewise represents a moiety which can be ortho-, meta- or para- with respect to the Y, and is preferably a $C_1$ to $C_6$ alkylene, and most preferably $C_2$ to $C_4$ alkyl. R is preferably a $C_1$ to $C_3$ alkyl R' is preferably cycloalkyl, most preferably cyclohexyl. R" is preferably hydrogen or $C_1$ to $C_3$ alkyl. X, as earlier mentioned, represents any pharmaceutically acceptable counteranion and is preferably a halogen, and most preferably chloride or bromide.

It can be seen that the compound as represented in the formula shown above is a quaternary ammonium ion salt form. If R" is hydrogen, the compound represents a tertiary amine salt. Other biologically acceptable salt forms of the compounds represented by the general formula above may of course be employed and are contemplated for use in this invention, as long as they have the necessary organic structure to provide the actively.

It is not known for certain whether every compound falling in the classes above described is psychoactive, but since representative members of the class have been found psychoactive because of their binding at sigma binding sites, it is likely that many more of those described are psychoactive. In particular, those compounds which have been tested as having a high degree of active sigma binding capability and are therefore useful antipsychotic drugs are N-cyclohexyl-N-ethyl 2-benzylamine, N-cyclohexyl-N-ethyl 2-phenylethylamine, bromhexine and suitable salt forms thereof.

The amount of the psychoactive drug administered will vary considerably but generally will fall within the dosage range of from 1 milligram to 500 milligrams, more commonly 1 milligram to 100 milligrams and more typically and therefore preferred within the range of 1 milligram to 10 milligrams. Frequency of dosing of course will vary from patient to patient and selection is well within the skill of the ordinary artisan.

The delivery system will of course include conventional pharmaceutical carriers. Such dosage forms can be administered in suitable suspensions, tablets or capsules. For example, pharmaceutical carriers which are liquid or solid may be used. The preferred liquid carrier is water. Flavoring materials may be included in the solutions as desired.

Solid pharmaceutical carriers such as starch, sugar, talc, mannitol and the like may be used to form powders. Mannitol is the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of one or more of the psychoactives, advisably as a nontoxic acid additional salt, and may be administered one or more at a time at regular intervals. Such unit dosage forms, however, should generally contain a concentration of 0.1% to 10% by weight of one or more of the active.

By way of example, a typical tablet may have the composition:

|  | Mg. |
|---|---|
| 1. Psychoactive drug | 12.5 |
| 2. Mannitol | 100 |
| 3. Stearic acid | 3 |

A granulation is made from the mannitol. The other ingredients are added to the dry granulation and then the tablets are punched.

Another tablet may have the composition:

|  | Mg. |
|---|---|
| 1. Psychoactive drug | 10 |
| 2. Starch U.S.P. | 57 |
| 3. Lactose U.S.P. | 73 |
| 4. Talc U.S.P. | 9 |
| 5. Stearic acid | 6 | powders 1, 2 and 3 are slugged, then granulated, mixed with 4 and 5, and tableted.

Capsules may be prepared by filling No. 3 hard gelatin capsules with the following ingredients, thoroughly mixed:

|  | Mg. |
|---|---|
| 1. Psychoactive drug | 5 |
| 2. Lactose U.S.P. | 200 |
| 3. Starch U.S.P. | 16 |
| 4. Talc U.S.P. | 8 |

The following examples are offered to further illustrate but not limit the invention. The first series of examples show preparation of compounds falling within the scope of the description herein presented for the active antipsychotic compounds of this invention and the second series of examples illustrate binding of those compounds, in particular N-cyclohexyl-N-ethyl benzylamine, N-cyclohexyl-N-ethyl 2-phenylethylamine, and bromhexine at sigma binding sites, a property of which is known to active investigators to indicate an active antipsychotic.

EXAMPLE 1

Preparation of N-cyclohexyl-N-ethylbenzylamine hydrochloride

A 100 ml round bottom flask fitted with a water cooled condenser and containing the following materials 4.15 g $K_2CO_3$ (2 eq., 0.03 moles) 2.26 ml N-ethylcyclohexylamine (1.91 g, 0.015 moles), 50 ml 4-methyl-2-pentanone, and 1.73 ml of benzyl chloride (1.9 g, 0.015 moles) was heated under reflux overnight. The reaction was monitored by thin layer chromatography and judged complete. The mixture was gravity filtered hot and the filtrate was concentrated on the rotary evaporator. A very fine crystalline material separated on cooling after concentration. The material was left overnight. A NaOH pellet was added followed by approximately 10 ml of water and the mixture was stirred for approximately 30 minutes. The liquid was extracted with chloroform, dried over sodium sulfate and concentrated on the rotovap. The oil was purified by flash chromatography using Davisil and 10% ethyl acetate/hexane as the eluent. The appropriate fractions were pooled and concentrated. 2.63 g of material. The oil was dissolved in anhydrous diethyl ether and $HC_1$ was bubbled into the liquid. Initial cloudiness dissipated and the material oiled out, absolute ethanol was added and the oil dissolved. (pH=2) The addition of acetone did not precipitate the salt. The solid eventually separated out and was vacuum filtered.

Recrystallization following treatment with charcoal from absolute ethanol resulted in the hydrochloride salt. mp 133.5°–135.0°C.

EXAMPLE 2

Preparation of N-cyclohexyl-N-ethyl 2-phenylethylamine hydrochloride

Into a 250 ml. round bottom flask fitted with a water cooled condenser and magnetic spin bar the following reagents were placed: N-ethyl-cyclohexylamine [3.82 g., 0.03 moles], potassium carbonate [6.8 g., 0.05 moles], 4-methyl-2-pentanone [100 ml.] and 2-phenylethyl bromide [5.55 g., 0.03 moles]. The combined reagents were stirred magnetically, while being heated to reflux, overnight. The solvent was removed by vacuum distillation to yield a brown oil. The product was purified by flash chromatography on silica gel using 10% ethyl acetate in hexane as the eluting solvent system. The product fractions from the chromatographic separation were combined and the solvent removed by vacuum distillation to yield a light yellow oil. The yellow oil was dissolved in anhydrous diethyl ether and hydrogen chloride gas was introduced to form a white hydrochloride salt. The hydrochloride salt was recrystallized from absolute ethanol to form a hygroscopic solid, m.p. 126° C. the nmr and ms analysis was consistent with the assigned structure.

EXAMPLE 3

The compound prepared in Example 1 was tested for sigma binding site inhibition in comparison with Haldol, a knows selective receptor for sigma binding sites. In particular, a radioligand of haldol was bound to sigma binding sites to provide radio labeled ligands at sigma binding receptor sites of tissue. In the tests, the compound of Example 1 was then added to the cell system to see how successfully it displaced the radioactive ligands at the sigma binding site. The higher the percentage of radio ligand displaced, the greater the percentage of specific binding at the sigma sites. The following table shows the results of testing the compound at Example 1 at molar concentrations of $10^{-9}$, $10^{-7}$ and $10^{-5}$.

TABLE 1

| Concentration | CONCENTRATION OF PSYCHOACTIVE DRUG OF EXAMPLE 1 | | VERIFICATION | |
|---|---|---|---|---|
| Con-centra-tion | % Displaced Haldol | % Sigma Site Binding | % Displaced Haldol | % Sigma Site Binding |
| $10^{-9}$ M | 27.5 | 72.5 | 22.5 | 77.5 |
| $10^{-7}$ M | 99.1 | 0.9 | 61.1 | 38.9 |
| $10^{-5}$ M | 96.0 | 4.0 | 86.7 | 13.3 |

Any number for a psychoactive drug over 50% is considered highly significant. By way of example, the following Table 2 illustrates a percentage of specific binding for certain known psychoactives capable of binding at other binding sites which are responsible for the undesirable side effects often associated with psychoactive agents.

TABLE 2

| Receptor/ Selectivity | Radioligand | Percent Inhibition (Average; N = 2) | | |
|---|---|---|---|---|
| | | $10^{-9}$ M | $10^{-7}$ M | $10^{-5}$ M |
| Biogenic Amines | | | | |
| Dopamine 1 | [$^3$H]-SCH 23390 | 3.2 | 5.9 | 10.7 |
| Dopamine 2 | [$^3$H]-Sulpiride | −1.4 | −1.5 | 14.8 |
| PCP | [$^3$H]-TCP | 9.4 | 7.1 | 25.1 |

[$^3$H]-TCP is a PCP derivative which selectively labels PCP site; PCP is phencyclidine)

Clearly, from the results of Tables 1 and 2, the drug of Example 1 selectively binds to the sigma binding site but is excluded from binding at dopaminergic receptors which are responsible for undesirable side effects when drug acts as an agonist at these sites.

EXAMPLE 4

The compound of Example 2 was tested in a similar fashion to that previously described in order to test comparison with Haldol or sigma binding site activity. For the compound of Example 2 the following table shows observed results.

TABLE 3

| Con-centra-tion | CONCENTRATION OF PSYCHOACTIVE DRUG OF EXAMPLE 1 | | VERIFICATION | |
|---|---|---|---|---|
| | % Displaced Haldol | % Sigma Site Binding | % Displaced Haldol | % Sigma Site Binding |
| $10^{-9}$ M | 43.2 | 56.8 | 33.9 | 66.1 |
| $10^{-7}$ M | 84.7 | 15.3 | 69.0 | 31.0 |
| $10^{-5}$ M | 107.6 | −7.6 | 91.7 | 8.3 |

From Tables 3 and 4, it is observed that the compound of Example 2 binds selectively to the sigma and PCP binding sites but only very weakly binds to the dopaminergic site. Therefore, the compound of Example 2 is expected to be a psychoactive drug with minimal undesirable side effects.

TABLE 4

| Receptor/ Selectivity | Radioligand | Percent Inhibition (Average; N = 2) | | |
|---|---|---|---|---|
| | | $10^{-9}$ M | $10^{-7}$ M | $10^{-5}$ M |
| Biogenic Amines | | | | |
| Dopamine 1 | [$^3$H]-SCH 23390 | 0.1 | 2.8 | 7.5 |
| Dopamine 2 | [$^3$H]-Sulpiride | 5.9 | 7.8 | 47.2 |
| PCP | [$^3$H]-TCP | 11.1 | 21.0 | 87.7 |

EXAMPLE 5

The following table illustrates testing of sigma binding capability of bromhexine. Again, the test protocol and procedure were as previously described.

TABLE 5

| Receptor/ Selectivity | Radioligand | Percent Binding | | |
|---|---|---|---|---|
| | | $10^{-9}$ M | $10^{-7}$ M | $10^{-5}$ M |
| sigma | [$^3$H]-DTG | 24.8 | 45.1 | 90.8 |

TABLE 6

| Biogenic Amines | | | | |
|---|---|---|---|---|
| Dopamine 1 | [$^3$H]-SCH 23390 | 3.9 | 10.8 | 17.5 |
| Dopamine 2 | [$^3$H]-Sulpiride | 5.6 | 4.5 | 11.9 |
| PCP | [$^3$H]-TCP | −13.6 | 0.2 | −2.5 |

Again, binding to dopaminergic and PCP sites is negligible as illustrated in Table 6. The Examples 1–6 and the data presented in the tables all illustrate that the compounds there prepared and bromhexine and psychoactive and bind to the sigma site which would make them useful antipsychotics. In each instance for the active compounds illustrated in the examples, by nature of the chemical structures they are expected to have few if any side affects in comparison with currently available psychoactives such as haldol.

It therefore can be seen that the invention accomplishes at least all of its stated objective.

What is claimed is:

1. A method of treating psychotic disorders, treatable by compounds having a strong degree of affinity for sigma binding cites, said method comprising:
    administering to a patient a small but pharmacologically active amount of a psychoactive drug selected from the group consisting of N-cyclohexyl-N-ethyl benzylamine, N-cyclohexyl-N-ethyl 2-phenylethylamine, and suitable salt forms thereof.

2. The method of claim 1 wherein the psychoactive drug is N-cyclohexyl-N-ethyl benzylamine.

3. The method of claim 1 wherein the psychoactive drug is N-cyclohexyl-N-ethyl 2-phenylethylamine.

4. The method of claim 1 wherein the drug is administered orally.

5. The method of claim 4 wherein the drug is administered in a dose of from 1 milligrams to about 500 milligrams.

6. The method of claim 5 wherein the drug is administered in a dose of from 1 milligram to about 100 milligrams.

7. The method of claim 6 wherein the drug is administered in a dose of from 1 milligrams to about 10 milligrams.

* * * * *